(12) United States Patent
Bös et al.

(10) Patent No.: US 6,310,208 B1
(45) Date of Patent: *Oct. 30, 2001

(54) SEROTONIN RECEPTOR BINDING BENZO [E]ISOINDOLES AND BENZO[H] ISOQUINOLINES

(75) Inventors: Michael Bös; Heinz Stadler, both of Rheinfelden (CH); Jürgen Wichmann, Steinen (DE)

(73) Assignee: Hoffmann-La Roche Inc., Nutley, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/003,446

(22) Filed: Jan. 6, 1998

(30) Foreign Application Priority Data

Jan. 8, 1997 (EP) .................................................. 97100172

(51) Int. Cl.[7] ...................... C07D 491/56; C07D 221/10; C07D 209/62; A61K 31/473; A61K 31/4035
(52) U.S. Cl. ........................... 546/65; 546/101; 548/427; 514/287; 514/290; 514/411
(58) Field of Search ..................... 546/101, 65; 514/290, 514/287, 411; 548/427

(56) References Cited

FOREIGN PATENT DOCUMENTS

| | | |
|---|---|---|
| 1 926 022 | 12/1969 | (DE) . |
| 0 201 085 | 5/1986 | (EP) . |
| 0 461 353 A1 | 3/1991 | (EP) . |
| 03101658-A2 * | 4/1991 | (JP) . |

OTHER PUBLICATIONS

Wijngaarden I et al. Recl. Trav. Chim. Pays–Bas. 112, 126–130, Feb. 1993.*

Branchek, T., et al., *Molecular Pharmacology*, 38:604–609 (1990).

Havlik, Sona and Stephen J. Peroutka, *Brain Research*, 584:191–196 (1992).

* cited by examiner

*Primary Examiner*—Evelyn Mei Huang
(74) *Attorney, Agent, or Firm*—George W. Johnston; William H. Epstein; Arthur D. Dawson

(57) ABSTRACT

Since the compounds in accordance with the invention can bind to serotonin receptors ($5HT_2$), they are especially suitable for the treatment or prevention of central nervous disorders such as depressions, bipolar disorders, anxiety states, sleep and sexual disorders, psychoses, schizophrenia, migraine and other conditions associated with cephalic pain or pain of a different kind, personality disorders or obsessive-compulsive disorders, social phobias or panic attacks, mental organic disorders, mental disorders in childhood, aggressivity, age-related memory disorders and behavioral disorders, addiction, obesity, bulimia etc., nervous system damage caused by trauma, stroke, neurodegenerative diseases etc.; cardiovascular disorders such as hypertension, thrombosis, stroke etc.; and gastrointestinal disorders such as dysfunction of the gastrointestinal tract motility.

13 Claims, No Drawings

SEROTONIN RECEPTOR BINDING BENZO [E]ISOINDOLES AND BENZO[H] ISOQUINOLINES

BACKGROUND OF THE INVENTION

Serotonin is a vasoconstrictor and neurotransmitter present in the brain, intestinal tissue and blood platelets. Regulation of the binding of serotonin can provide a method of treatment and prevention of a variety of illnesses including central nervous disorders, personality disorders, nervous system damage, cardiovascular disorders and gastrointestinal disorders. The compounds of this invention bind to serotonin receptors and are suitable for treatment of many therapeutic indications including those listed above.

SUMMARY OF THE INVENTION

The present invention relates to tricyclic compounds. In particular, it relates to benzo[e]isoindoles and benzo[h] isoquinolines of the general formula

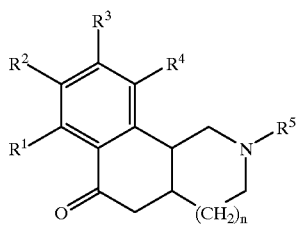

I wherein
- $R^1$–$R^4$ each independently signify hydrogen, halogen, hydroxy, lower alkyl, lower-alkoxy or phenyl or $R^2$ and $R^3$ together represent —O—CH$_2$—O—;
- $R^5$ signifies hydrogen, lower-alkyl or benzyl; and
- n signifies 0 or 1 as well as pharmaceutically acceptable acid addition salts of the compounds of formula I, with the exception of racemic 2-methyl-1,3,4,4a,5,10b-hexahydro-2H-benzo[h]isoquinolin-6-one.

The compounds of formula I are novel with the exception of rac. 2-methyl-1,3,4,4a,5,10b-hexahydro-2H-benzo[h] isoquinolin-6-one (DE 19 26 022). The compounds described in this Offenlegungsschrift have antiphlogistic properties for use against inflammations as well as oedemas following contusions, distortions or fractures.

Since the compounds in accordance with the invention can bind to serotonin receptors (5HT$_2$), they are especially suitable for the treatment or prevention of central nervous disorders such as depressions, bipolar disorders, anxiety states, sleep and sexual disorders, psychoses, schizophrenia, migraine and other conditions associated with cephalic pain or pain of a different kind, personality disorders or obsessive-compulsive disorders, social phobias or panic attacks, mental organic disorders, mental disorders in childhood, aggressivity, age-related memory disorders and behavioral disorders, addiction, obesity, bulimia etc., nervous system damage caused by trauma, stroke, neurodegenerative diseases etc.; cardiovascular disorders such as hypertension, thrombosis, stroke etc; and gastrointestinal disorders such as dysfunction of the gastrointestinal tract motility.

Objects of the present invention include: compounds of formula I and pharmaceutically acceptable acid addition salts thereof, their racemic mixtures and the corresponding enantiomers thereof and as pharmaceutically active substances; the manufacture of these compounds and salts; medicaments containing a compound of formula I or a pharmaceutically acceptable acid addition salt thereof; the production of such medicaments; and the use of the compounds of formula I and their pharmaceutically acceptable salts in the control or prevention of illnesses, especially of illnesses and disorders of the aforementioned kind, and, respectively, for the production of corresponding medicaments. Only the named known compound itself is excluded from the objects of the present invention as previously defined.

DETAILED DESCRIPTION OF THE INVENTION

The following definitions of the general terms are used in the present specification and apply irrespective of whether the terms appear alone or in combination.

As used herein, the term "lower" denotes residues with a maximum of 7, preferably up to 4, carbon atoms.

The term "alkyl" denotes straight-chain or branched saturated hydrocarbon residues such as methyl, ethyl, propyl, isopropyl, n-butyl, 2-butyl or t-butyl.

The term "alkoxy" denotes an alkyl group bonded via an oxygen atom, such as methoxy, ethoxy, propoxy, isopropoxy or butoxy.

The term "halogen" can signify Cl, Br, F or I.

The term "pharmaceutically acceptable acid addition salts" embraces salts with inorganic or organic acids, such as hydrochloric acid, hydrobromic acid, nitric acid, sulphuric acid, phosphoric acid, citric acid, formic acid, fumaric acid, maleic acid, acetic acid, succinic acid, tartaric acid, methanesulphonic acid, p-toluenesulphonic acid and the like.

Those compounds in which $R^4$ signifies hydrogen, $R^5$ signifies methyl and n signifies 1 are preferred, and particularly preferred are compounds wherein further, $R^1$ signifies hydrogen, hydroxy, halogen or methyl, $R^2$ signifies hydrogen or ethyl and $R^3$ signifies hydrogen, methyl or methoxy.

Some particularly preferred representatives of the class of substances defined by general formula I above are:
- rac-trans-8-Ethyl-7-hydroxy-9-methoxy-2-methyl-1,3,4, 4a, 5,10b-hexahydro-2H-benzo[h]isoquinolin-6-one;
- rac-cis-7-methoxy-2-methyl-1,3,4,4a,5,10b-hexahydro-2H-benzo[h]isoquinolin-6-one;
- rac-cis-2,9-dimethyl-1,3,4,4a,5,10b-hexahydro-2H-benzo [h]isoquinolin-6-one;
- rac-cis-7-chloro-2-methyl-1,3,4,4a,5,10b-hexahydro-2H-benzo[h]isoquinolin-6-one;
- rac-cis-7-fluoro-2-methyl-1,3,4,4a,5,10b-hexahydro-2H-benzo[h]isoquinolin-6-one;
- rac-cis-2,7,9-trimethyl-1,3,4,4a,5,10b-hexahydro-2H-benzo[h]isoquinolin-6-one;
- (+)-trans-8-ethyl-7-hydroxy-9-methoxy-2-methyl-1,3,4, 4a, 5,10b-hexahydro-2H-benzo[h]isoquinolin-6-one;
- (+)-cis-2,7-dimethyl-1,3,4,4a,5,10b-hexahydro-2H-benzo [h]isoquinolin-6-one;
- (+)-cis-2,7,9-trimethyl-1,3,4,4a,5,10b-hexahydro-2H-benzo[h]isoquinolin-6-one and
- (+)-cis-2-methyl-1,3,4,4a,5,10b-hexahydro-2H-benzo[h] isoquinolin-6-one.

Compounds of general formula I as well as their pharmaceutically acceptable acid addition salts can be manufactured in accordance with the invention in manners set forth below:

a) cyclizing a compound of the general formula (II)

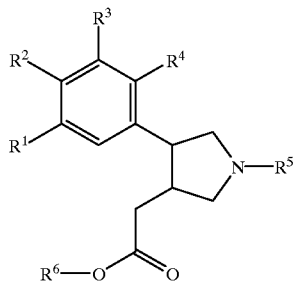

wherein R⁶ signifies lower-alkyl, to a compound of the general formula (IA)

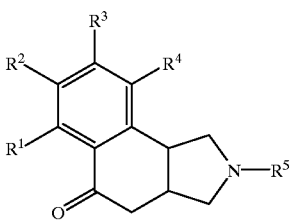

or b) cyclizing a compound of the general formula (III)

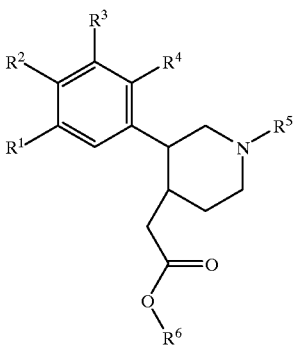

to a compound of the general formula (IB)

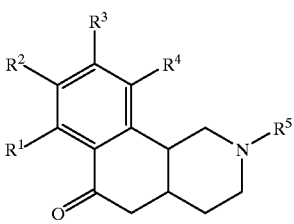

or c) alkylating or benzylating a compound of general formula I in which $R^5$ signifies hydrogen, or
d) desalkylating a compound of general formula I in which $R^5$ signifies alkyl or benzyl, or
e) in a compound of general formula I in which at least one of $R^1$–$R^4$ signifies an alkoxy group, converting this/these into (a) hydroxy group(s), and
f) if desired, converting the compound of formula I obtained into a pharmaceutically acceptable acid addition salt.

In accordance with process variant a) the cyclization of a correspondingly substituted acetic acid ester of general formula II can be effected with polyphosphoric acid at a reaction temperature of about 120° C. Toluene is especially suitable as the solvent. Another cyclization method comprises the reaction of a corresponding ester with phosphorus oxychloride in the presence of a strong base.

The cyclization of a compound of formulas III to compounds of formulas IB (see Scheme 2) in accordance with variant b) is effected analogously to variant a). A mixture of polyphosphoric acid and toluene is reacted with a corresponding acetic acid ester for several hours at about 120° C. and the product is subsequently purified according to known methods.

In accordance with process variant c) the alkylation or benzylation at the N atom of the ring nitrogen is effected with an alkyl or benzyl halide, preferably methyl bromide, ethyl bromide, propyl bromide or benzyl bromide. Conveniently, a compound of general formula I in which $R^5$ signifies hydrogen is reacted with an aforementioned alkyl or benzyl halide in the presence of an alkaline salt, for example $K_2CO_3$, in anhydrous DMF at about 125° C.

The desalkylation at the N atom of the ring nitrogen is effected in accordance with process variant d) by treating a compound of general formula I in which $R^5$ signifies alkyl in anhydrous chloroform and at room temperature with a cyanogen halide, preferably cyanogen bromide, subsequently heating under reflux and, after concentration under reduced pressure, again boiling under reflux with hydrochloric acid for several hours. Another possibility comprises treatment of a corresponding compound with 2,2,2-trichloroethyl chloroformate.

In accordance with process variant e) a compound of general formula I in which one of $R^1$–$R^4$ signifies an alkoxy group is converted into a compound of formula I in which one of $R^1$–$R^4$ signifies a hydroxy group. This is conveniently effected by converting the corresponding compound of formula I into the hydrochloride and subsequently converting the latter into the corresponding hydroxy compound at about −70° C. using a $BBr_3$ solution in methylene chloride.

It has been found that these compounds and their acid addition salts are especially well suited for a pharmaceutical use. The addition of the corresponding acids to the compounds of formula I is conveniently effected prior to their final isolation at the conclusion of the described manufacturing variants.

The compounds required as precursors for the manufacture of the compounds of formula I can be prepared according to Schemes 1 and 2 infra.

Scheme 1 describes the manufacture of the compounds of formula I in which n signifies 0. The steps for the synthesis are described in detail in Example 1a–1h as an example for the manufacture of cis-7-ethyl-6-hydroxy-8-methoxy-2-methyl-1,2,3,3a,4,9b-hexahydro-benzo[e]isoindol-5-one.

The manufacture of compounds of general formula I in which n signifies 1 is set forth in Formula Scheme 2. A detailed description for the manufacture of compounds of formulas IBa and IBb starting from a compound of general formula IV is described in Example 8a—8i as a concrete example for trans-8-ethyl-7-hydroxy-9-methoxy-2-methyl-1,3,4,4a,5,10b-hexahydro-2H-benzo[h]isoquinolin-6-one.

Scheme 1
(according to Example 1)
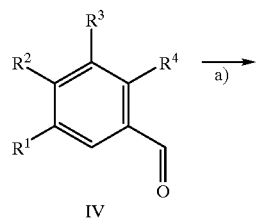
IV
a)
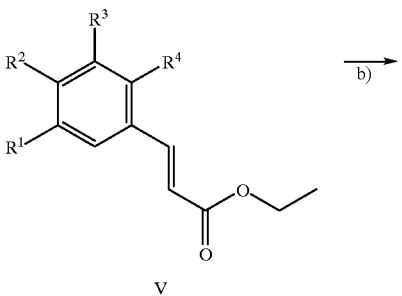
V
b)
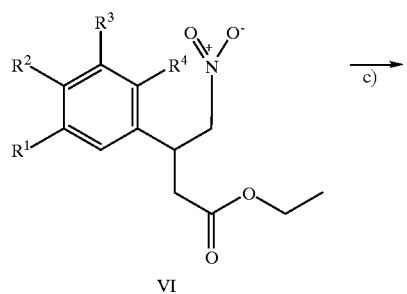
VI
c)
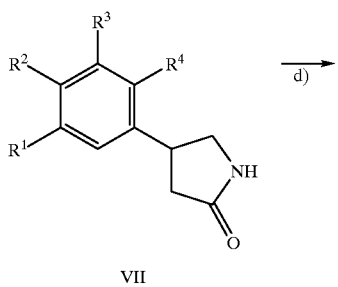
VII
d)
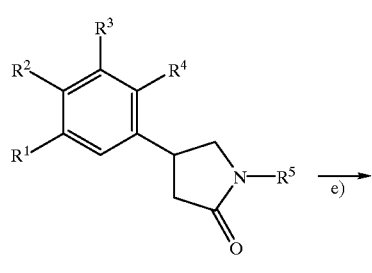
VIII
e)
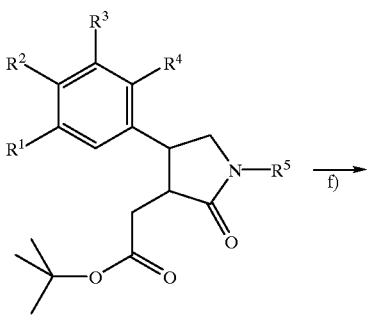
IX
f)
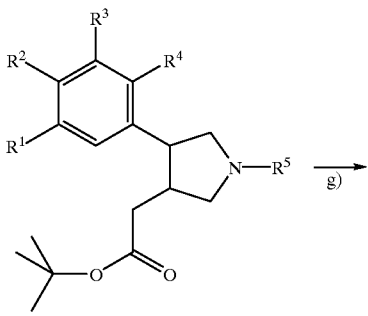
IIa
g)
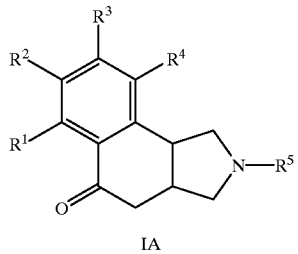
IA
Scheme 2
(according to Example 8)
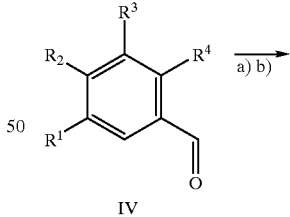
IV
a) b)
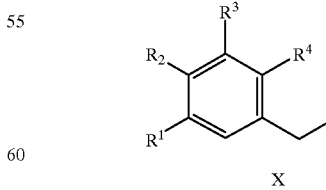
X
c1) c2)

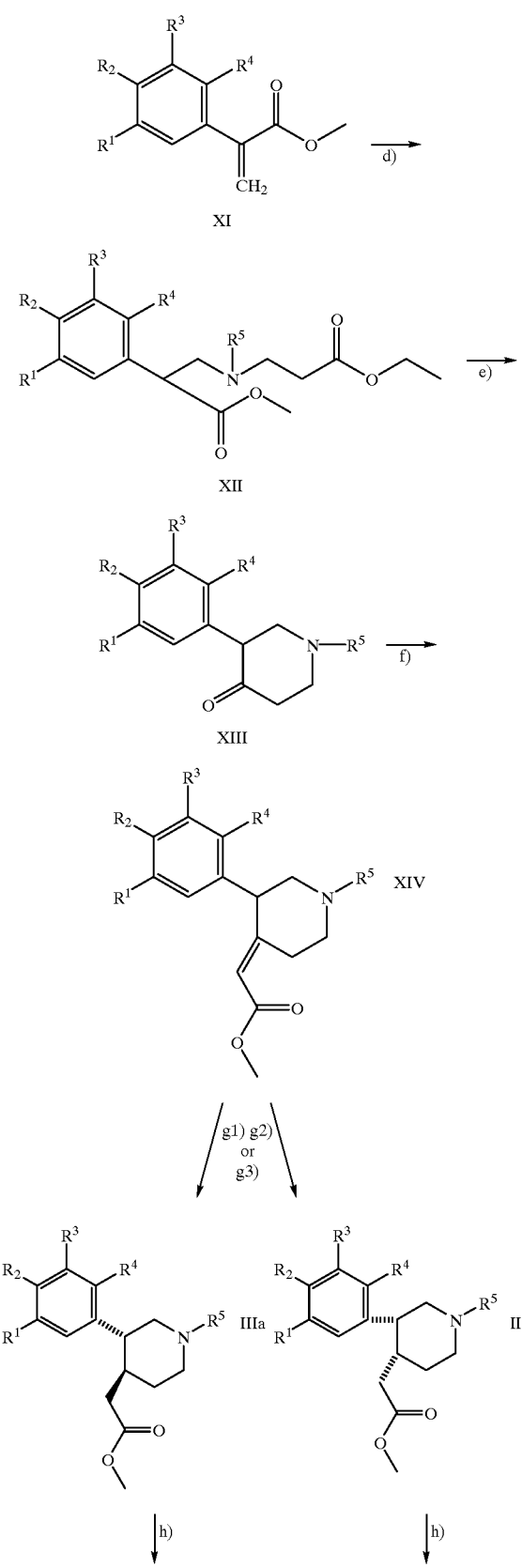

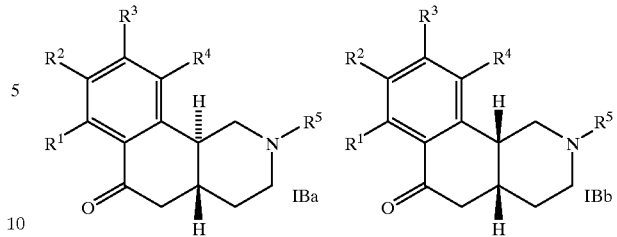

The binding of compounds of formula I, in accordance with the invention, to the serotonin receptors was determined in vitro by standard methods. The compounds were investigated in accordance with the assays given hereinafter:

a) for the binding to the $5HT_{2C}$ receptor in accordance with the [3H]-5-HT binding assay according to the method of S. J. Peroutka et al., Brain Research 584, 191–196 (1992).

b) for the binding to the $5HT_{2A}$ receptor in accordance with the [3H]-DOB binding assay according to the method of T. Branchek et al., Molecular Pharmacology 38, 604–609 (1990).

The (Pki values Pki=$-\log_{10}$ Ki) of the test compounds are given. The ki value is defined by the following formula:

$$Ki = \frac{IC_{50}}{1 + \frac{[L]}{K_D}}$$

in which the $IC_{50}$ values are those concentrations of test compounds in nM by which 50% of the receptor-bound ligands are displaced. [L] is the concentration of ligand and the $K_D$ value is the dissociation constant of the ligand.

The thus-determined activity of some compounds in accordance with the invention will be evident from the following Table:

|  |  | Test method | |
|---|---|---|---|
|  |  | a | b |
| Compound | Example | $5HT_{2A}$ | $5HT_{2C}$ |
| A | 8 | 6.90 | 7.98 |
| B | 13 | <5 | 7.22 |
| C | 15 | 5.17 | 7.26 |
| D | 17 | 6.2 | 7.86 |
| E | 31 | <5 | 7.57 |
| F | 42 | 5.96 | 7.61 |
| G | 43 | 7.21 | 8.47 |
| H | 44 | <5 | 7.00 |
| I | 46 | <5 | 7.84 |
| J | 47 | 5.83 | 7.32 |
| K | 48 | 5.13 | 8.14 |

A = rac-trans-8-Ethyl-7-hydroxy-9-methoxy-2-methyl-1,3,4,4a,5,10b-hexahydro-2H-benzo[h]isoquinolin-6-one
B = rac-7-Methoxy-2-methyl-1,3,4,4a,5,10b-hexahydro-2H-benzo[h]isoquinolin-6-one
C = rac-cis-2,9-Dimethyl-1,3,4,4a,5,10b-hexahydro-2H-benzo[h]isoquinolin-6-one
D = rac-cis-7-Chloro-2-methyl-1,3,4,4a,5,10b-hexahydro-2H-benzo[h]isoquinolin-6-one
E = rac-cis-7-Fluoro-2-methyl-1,3,4,4a,5,10b-hexahydro-2H-benzo[h]isoquinolin-6-one
F = rac-cis-2,7,9-Trimethyl-1,3,4,4a,5,10b-hexahydro-2H-benzo[h]isoquinolin-6-one
G = (+)-trans-8-Ethyl-7-hydroxy-9-methoxy-2-methyl-1,3,4,4a,5,10b-hexahydro-2H-benzo[h]isoquinolin-6-one -continued

| | | Test method | |
|---|---|---|---|
| Compound | Example | a<br>5HT$_{2A}$ | b<br>5HT$_{2C}$ |

H = (+)-cis-7-Methoxy-2-methyl-1,3,4,4a,5,10b-hexahydro-2H-benzo[h]isoquinolin-6-one
I = (+)-cis-2,7-Dimethyl-1,3,4,4a,5,10b-hexahydro-2H-benzo[h]isoquinolin-6-one
J = (+)-cis-2,7,9-Trimethyl-1,3,4,4a,5,10b-hexahydro-2H-benzo[h]isoquinolin-6-one
K = (+)-cis-2-Methyl-1,3,4,4a,5,10b-hexahydro-2H-benzo[h]isoquinolin-6-one The compounds of formula I and the pharmaceutically acceptable acid addition salts of the compounds of formula I can be used as medicaments, e.g. in the form of pharmaceutical preparations. The pharmaceutical preparations can be administered orally, e.g. in the form of tablets, coated tablets, dragees, hard and soft gelatin capsules, solutions, emulsions or suspensions. The administration can, however, also be effected rectally, e.g. in the form of suppositories, parenterally, e.g. in the form of injection solutions, or nasally.

The compounds of formula I and the pharmaceutically acceptable acid addition salts of the compounds of formula I can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active substance no carriers are, however, usually required in the case of soft gelatin capsules. Suitable carriers for the production of solutions and syrups are, for example, water, polyols, glycerol, vegetable oils and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable acid addition salt thereof and a therapeutically inert carrier are also an object of the present invention, as is a process for their production which comprises bringing one or more compounds of formula I and/or pharmaceutically acceptable acid addition salts into a galenical administration form together with one or more therapeutically inert carriers.

In accordance with the invention, compounds of general formula I as well as their pharmaceutically acceptable acid addition salts can be used in the treatment or prevention of central nervous disorders such as depressions, bipolar disorders, anxiety states, sleep and sexual disorders, psychoses, schizophrenia, migraine and other conditions associated with cephalic pain or pain of a different kind, personality disorders or obsessive-compulsive disorders, social phobias or panic states, mental organic disorders, mental disorders in childhood, aggressivity, age-related memory disorders and behavioral disorders, addiction, obesity, bulimia etc.; nervous system damage caused by trauma, stroke, neurodegenerative diseases etc.; cardiovascular disorders such as hypertension, thrombosis, stroke etc.; and gastrointestinal disorders such as dysfunction of the gastrointestinal tract motility and, respectively, for the production of corresponding medicaments. The dosage can vary within wide limits and will, of course, be fitted to the individual requirements in each particular case. In the case of oral administration the dosage lies in a range of about 0.01 mg to about 500 mg of a compound of general formula I or the corresponding amount of a pharmaceutically acceptable acid addition salt thereof, although the upper limit can also be exceeded when this is found to be indicated. The daily dosage can be administered as a single dosage or divided into several single dosages.

The following Examples illustrate the present example invention in more detail. However, they are not intended to limit its scope in any manner. All temperatures are given in degrees Celsius.

EXAMPLE 1 cis-7-Ethyl-6-hydroxy-8-methoxy-2-methyl-1,2,3,3a,4,9b-hexahydro-benzo[e]isoindol-5-one a) 39.4 ml (63 mmol) of a 1.6N solution of n-butyllithium in hexane were added over a period of 15 minutes while stirring at −40° to a suspension of 28.3 g (66 mmol) of ethoxycarbonylmethyl-triphenylphosphonium bromide in 200 ml of tetrahydrofuran. The reaction mixture was stirred at 0° for one hour, cooled to −70° and treated dropwise over 30 minutes with a solution of 11.6 g (60 mmol) of 4-ethyl-3,5-dimethoxybenzaldehyde in 100 ml of tetrahydrofuran. Subsequently, the mixture was stirred at room temperature for a further 16 hours, poured into 600 ml of saturated sodium chloride solution and extracted twice with 800 ml of diethyl ether each time. The combined organic phases were washed once with 600 ml of saturated sodium chloride solution, dried (MgSO$_4$) and concentrated in a vacuum. The crude product obtained was purified by column chromatography on silica gel (hexane/ethyl acetate 5:1). 12.5 g (79%) of ethyl 3-(4-ethyl-3,5-dimethoxy-phenyl)-acrylate were obtained as a white solid.

b) A mixture of 12.5 g (47.3 mmol) of ethyl (4-ethyl 3,5-dimethoxy-phenyl)-acrylate, 40 ml of nitromethane and 10 ml of a 40% solution of Triton B in methanol was stirred at 600 over 15 hours. Subsequently, the reaction mixture was poured on to 50 ml of ice and 50 ml of 3N sulfuric acid and extracted twice with 300 ml of ethyl acetate each time. The combined organic phases were washed twice with 100 ml of saturated sodium chloride solution each time, dried (MgSO$_4$) and concentrated in a vacuum. 15.1 g (98%) of ethyl 3-(4-ethyl-3,5-dimethoxy-phenyl)-4-nitro-butanoate were obtained as a yellow oil.

c) 15.1 g (46.4 mmol) of ethyl 3-(4-ethyl-3,5-dimethoxy-phenyl)-4-nitro-butanoate dissolved in 300 ml of ethanol were hydrogenated on Raney-nickel while stirring over a period of 2.5 hours. The catalyst was filtered off, washed several times with ethanol and the combined ethanol phases were concentrated in a vacuum to a volume of 200 ml. The reaction mixture was treated with 1.7 g of sodium acetate and 50 mg of p-toluenesulphonic acid and heated under reflux over 24 hours. Subsequently, the mixture was concentrated in a vacuum and the residue was purified by column chromatography on silica gel (methylene chloride/methanol 19:1). 8.85 g (76%) of 4-(4-ethyl-3,5-dimethoxy-phenyl)-pyrrolidin-2-one were obtained as a beige solid with m.p. 156°.

d) 3.12 g (78 mmol) of a sodium hydride dispersion (60% in oil) were added using a spatula and while stirring to a suspension of 8.85 g (35.5 mmol) of 4-(4-ethyl-3,5-dimethoxy-phenyl)-pyrrolidin-2-one in 250 ml of tetrahydrofuran and 2 ml of dimethylformamide and the mixture was stirred at room temperature for a further hour. Thereafter, the reaction mixture was treated with 3.52 ml (106.5 mmol) of methyl iodide and left to stir at room temperature for a further 16 hours. Subsequently, the reaction mixture was poured on to 400 ml of ice-water and extracted twice with 600 ml of ethyl acetate each time. The combined organic phases were washed twice with 300 ml of saturated sodium chloride solution each time, dried ($MgSO_4$) and concentrated in a vacuum. The crude product was purified by column chromatography on silica gel (methylene chloride/methanol 39:1). 8.08 g (86%) of 4-(4-ethyl-3,5-dimethoxy-phenyl)-1-methyl-pyrrolidin-2-one were obtained as a beige solid.

e) A solution of LDA in 20 ml of anhydrous tetrahydrofuran, freshly prepared at 0° from 1.35 ml (9.5 mmol) of diisopropylamine and 5.93 ml (9.5 mmol) of a 1.6N solution of n-butyllithium in hexane, was added dropwise while stirring to a solution, cooled to −70°, of 2 g (7.6 mmol) of 4-(4-ethyl-3,5-dimethoxy-phenyl)-1-methyl-pyrrolidin-2-one in 20 ml of anhydrous tetrahydrofuran. The mixture was stirred at −70° for a further 30 minutes and subsequently a solution of 1.23 ml (8.35 mmol) of tert.-butyl bromoacetate in 20 ml of tetrahydrofuran was added dropwise thereto over 30 minutes. Thereafter, the mixture was stirred for a further 22 hours without removal of the cooling bath, with the temperature slowly coming to room temperature. The mixture was poured on to 150 ml of ice-water and extracted twice 250 ml of ethyl acetate each time. The combined organic phases were washed once with saturated sodium chloride solution, dried ($MgSO_4$) and concentrated in a vacuum. The crude product obtained was purified by column chromatography on silica gel (ethyl acetate). In addition to 0.54 g of educt there were obtained 1.23 g (43% and, respectively, 58% based on the conversion) of tert-butyl(4-(4-ethyl-3,5-dimethoxy-phenyl)-1-methyl-2-oxo-pyrrolidin-3-yl)-acetate as a pale yellow oil.

f) A solution of 1.23 g (3 26 mmol) of tert-butyl (4-(4-ethyl-3,5-dimethoxy-phenyl)-1-methyl-2-oxo-pyrrolidin-3-yl)-acetate in 20 ml of tetrahydrofuran was treated at room temperature while stirring with 32.6 ml (32.6 mmol) of a 1M borane-THF complex solution and subsequently heated under reflux for 7 hours. Thereafter the reaction mixture was cooled to 0°, 10 ml of methanol were slowly added dropwise thereto and the mixture was concentrated in a vacuum. The residue was purified by column chromatography on silica gel (ethyl acetate). 0.9 g (76%) of tert.-butyl 4-(4-ethyl-3,5-dimethoxy-phenyl)-1-methyl-2-oxo-pyrrolidin-3-yl)-acetate was obtained as a colorless oil.

g) A mixture of 1.08 g (2.97 mmol) of tert.-butyl 4-(4-ethyl-3,5-dimethoxy-phenyl)-1-methyl-2-oxo-pyrrolidin-3-yl)-acetate and 11 g of polyphosphoric acid was stirred at 120° over 75 minutes. The reaction mixture was subsequently adjusted to pH 6 with 28% NaOH and sodium acetate and extracted three times with 100 ml of methylene chloride each time. The combined organic phases were washed once with 50 ml of saturated sodium chloride solution, dried ($MgSO_4$) and concentrated in a vacuum. The crude product obtained was purified by column chromatography on silica gel (methylene chloride/methanol/$NH_4OH$ 15:1:0.1). 0.4 g (49%) of cis 7-ethyl-6-hydroxy-8-methoxy-2-methyl-1,2,3,3a,4,9b-hexahydro-benzo[e]isoindol-5-one was obtained as a colorless oil.

h) 168 mg (1.45 mmol) of fumaric acid and 50 ml of diethyl ether were added while stirring to a solution of 0.4 g (1.45 mmol) of cis-7-ethyl-6-hydroxy-8-methoxy-2-methyl-1,2,3,3a,4,9b-hexahydro-benzo[e]isoindol-5-one in 0.5 ml of ethanol. The mixture was stirred at room temperature for a further 17 hours and the solid was subsequently filtered off. 0.55 g (97%) of 7-ethyl-6-hydroxy-8-methoxy-2-methyl-1,2,3,3a,4,9b-hexahydro-benzo[e]isoindol-5-one fumarate (1:1) was obtained as a white solid with m.p. 195°.

EXAMPLE 2 cis-7-Ethyl-6,8-dimethoxy-2-methyl-1,2,3,3a,4,9b-hexahydro-benzo[e]isoindol-5-one a) A mixture of 150 mg (0.41 mmol) of (4-(4-ethyl-3,5-dimethoxy-phenyl)-1-methyl-pyrrolidin-3-yl)-acetate, 1.5 ml trifluoroacetic acid and 0.15 ml of trifluoroacetic acid anhydride was stirred at room temperature over 2 hours. The reaction mixture was subsequently poured on to 50 ml of ice-water, made basic with 28% NaOH and extracted twice with 100 ml of methylene chloride each time. The combined organic phases were washed once with 50 ml of saturated sodium chloride solution, dried ($MgSO_4$) and concentrated in a vacuum. The crude product obtained was purified by column chromatography on silica gel (methylene chloride/methanol/$NH_4OH$ 15:1:0.1). 15 mg (13%) of cis-7-ethyl-6,8-dimethoxy-2-methyl-1 ,2,3,3a,4,9b-hexahydro-benzo[e]isoindol-5-one were obtained as a colorless oil.

b) 6 mg (0.05 mmol) of fumaric acid 10 ml of hexane and 10 ml of diethyl ether were added while stirring to a solution of 15 mg (0.05 mmol) of cis-7-ethyl-6,8-dimethoxy-2-methyl-1,2,3,3a,4,9b-hexahydro-benzo[e]isoindol-5-one in 0.1 ml of ethanol. The mixture was stirred at room temperature for a further 2 hours and the solid was subsequently filtered off. 15 mg (75%) of cis-7-ethyl-6,8-dimethoxy-2-methyl-1,2,3,3a, 4,9b-hexahydro-benzo[e]isoindol-5-one fumarate (1:1) were obtained as a beige solid with m.p. 148°.

EXAMPLE 3 cis-8-Methoxy-2-methyl-1,2,3,3a,4,9b-hexahydro-benzo[e]-isoindol-5-one

In an analogous manner to that described in Example 1 d)–h), from 4-(3-methoxy-phenyl)-pyrrolidin-2-one there was obtained cis-8-methoxy-2-methyl-1,2,3,3a,4,9b-hexahydro-benzo[e]isoindol-5-one fumarate (1:1) as a white solid with m.p. 193°.

EXAMPLE 4 cis-2,8-Dimethyl-1,2,3,3a,4,9b-hexahydro-benzo[e]isoindol-5-one

In an analogous manner to that described in Example 1 b)–h), from ethyl 3-(3-methyl-phenyl)-acrylate there was obtained cis-2,8-dimethyl-1,2,3,3a,4,9b-hexahydro-benzo[e]isoindol-5-one fumarate (1:1) as a white solid with m.p. 153°.

EXAMPLE 5 cis-8-Chloro-2-methyl-1,2,3,3a,4,9b-hexahydro-benzo[e]isoindol-5-one

In an analogous manner to that described in Example 1 b)–h), from ethyl 3-(3-chloro-phenyl)-acrylate there was obtained cis-8-chloro-2-methyl-1,2,3,3a,4,9b-hexahydro-benzo[e]isoindol-5-one fumarate (1:0.5) as a white solid with m.p. 213°.

EXAMPLE 6 cis-2-Methyl-1,2,3,3a,4,9b-hexahydro-benzofelisoindol-5-one

In an analogous manner to that described in Example 1e)–h), from 1-methyl-4-phenyl-pyrrolidin-2-one there was obtained cis-2-methyl-1,2,3,3a,4,9b-hexahydro-benzo[e]isoindol-5-one fumarate (1:0.5) as a white solid with m.p. 203°.

EXAMPLE 7 cis-7-Methoxy-2-methyl-1,2,3,3a,4,9b-hexahydro-benzo[e]-isoindol-5-one

In an analogous manner to that described in Example 1 e)–h), from 4-(4-methoxy-phenyl)-1-methyl-pyrrolidin-2-one there was obtained cis-7-methoxy-2-methyl-1,2,3,3a,4,9b-hexahydro-benzo[e]isoindol-5-one fumarate (1:1) as a white solid with m.p. 173°.

EXAMPLE 8 trans-8-ethyl-7-hydroxy-9-methoxy-2-methyl-1,3.4.4a,5.10b-hexahydro-2-H-benzo[h]isoquinolin-6-one a) 130 ml of a 40% solution of benzyltrimethylammonium hydroxide in methanol (Triton B) were added to a solution of 126.5 g (651.2 mmol) of 4-ethyl-3,5-dimethoxy-benzaldehyde and 80.89 g (651.2 mmol) of methyl methylthiomethyl sulphoxide in 300 ml of tetrahydrofuran and the mixture was heated at reflux for 5 hours. After the addition of 300 ml of methylene chloride the mixture was extracted with 200 ml of 0.5M sulphuric acid. The organic phase was dried ($MgSO_4$), filtered and evaporated. Chromatography of the resulting residue (silica gel, ethyl acetate/hexane 1:1) yielded 134.6 g (69%) of (E)-2-ethyl-5-(2-methylsulphanyl-2-methylsulphinyl-vinyl)-1,3-dimethoxybenzene as a colorless oil, which gave colorless crystals of m.p. 82–83° by crystallization from hexane.

b) 400 ml of a concentrated methanolic hydrochloric acid solution were added to a solution of 130.0 g (433 mmol) of (E)-2-ethyl-5-(2-methylsulphanyl-2-methylsulphinyl-vinyl)-1,3-dimethoxybenzene in 200 ml of methanol and the mixture was stirred at 50° for 4 hours. Subsequently, the methanol was evaporated and the residue was partitioned between 300 ml of methylene chloride and 200 ml of sat. sodium hydrogen carbonate solution. The aqueous phase was washed twice with 200 ml of methylene chloride and the organic phases were dried ($MgSO_4$), filtered and evaporated. Chromatography of the residue (silica gel, ethyl acetate/hexane 1:9) yielded 100.5 g (94%) of methyl (4-ethyl-3,5-dimethoxy-phenyl)-acetate as a colorless wax, Rf=0.345 (silica gel, ethyl acetate/hexane 1:9).

c 1) A solution of 80.43 g (337.5 mmol) of methyl (4-ethyl-3,5-dimethoxy-phenyl)-acetate in 400 ml of toluene was added dropwise to a suspension of 22.1 g (506 mmol) of NaH (55% in mineral oil) in 400 ml of tetrahydrofuran and 40.86 g (346 mmol) of dimethyl oxalate and the mixture was stirred at room temperature for 65 hours. The reaction mixture was poured on to 300 ml of ice-water and washed twice with 250 ml of diethyl ether. The aqueous phase was adjusted to pH 1 with 25% HCl and extracted three times with 300 ml of diethyl ether. The combined phases were dried ($MgSO_4$), filtered and evaporated. The thus-obtained dimethyl 2-(4-ethyl-3,5-dimethoxy-phenyl)-3-oxo-succinate (101.9 g, 314.3 mmol) was suspended in 150 ml of water and treated with 61 ml (812 mmol) of formaldehyde solution (37% in water). Subsequently, a solution of 43.4 g of potassium carbonate in 150 ml of water was slowly added dropwise thereto and the mixture was stirred at room temperature for 12 hours and then extracted three times with 250 ml of diethyl ether. The combined organic phases were dried ($MgSO_4$), filtered and evaporated. Chromatography of the resulting residue (silica gel, hexane/methylene chloride 1:2) gave 44.5 g (53%) of methyl 2-(4-ethyl-3,5-dimethoxy-phenyl)-acrylate as a colorless wax, Rf=0.635 (silica gel, methylene chloride/hexane 2:1).

c 2) 18.9 g (630 mmol) of paraformaldehyde, 92.8 g (672 mmol) of potassium carbonate and 3.1 g (8.4 mmol) of tetrabutylammonium iodide were added to a solution of 100 g (420 mmol) of methyl 2-(4-ethyl-3,5-dimethoxy-phenyl)-acrylate in 200 ml of toluene and the mixture was heated to 80° for 6 hours and then cooled and treated with 150 ml of water. The phases were separated and the aqueous phase was extracted twice with 120 ml of toluene. The combined organic phases were dried ($MgSO_4$), filtered and evaporated. Chromatography of the resulting residue (silica gel, hexane/methylene chloride 2:1) gave 70.5 g (67%) of methyl 2-(4-ethyl-3,5-dimethoxy-phenyl)-acrylate as a colorless wax, Rf=0.635 (silica gel, methylene chloride/hexane 2:1).

d) A solution of 78.4 g (313 mmol) of methyl 2-(4-ethyl-3,5-dimethoxy-phenyl)-acrylate and 47.7 g (364 mmol) of ethyl 3-methylamino-propionate was stirred at room temperature for 48 hours. Chromatography of the reaction mixture (silica gel, ethyl acetate/hexane 1:1) and crystallization from hexane gave 71.1 g (59%) of methyl 3-[(2-ethoxycarbonyl-ethyl)-methyl-amino]-2-(4-ethyl-3,5-dimethoxy-phenyl)-propionate as colorless crystals of m.p. 74–75°.

e) A solution of 53.51 g (140.3 mmol) of methyl 3-[(2-ethoxycarbonyl-ethyl)-methyl-amino]-2-(4-ethyl-3,5-dimethoxyphenyl)-propionate in 150 ml of toluene was added dropwise at 80° to a suspension of 11.62 g (266.3 mmol) of sodium hydride (55% in mineral oil) in 150 ml of toluene and the mixture was subsequently heated at reflux for 15 hours. The solution was cooled to room temperature and adjusted to pH 1 with 6N hydrochloric acid. The toluene was separated and extracted once with 150 ml of 6N hydrochloric acid. The acidic phases were heated at reflux for 20 hours. After cooling to room temperature the mixture was adjusted to pH 14 with 28% NaOH and extracted three times with 250 ml of methylene chloride. The organic phases were washed once with 200 ml of water and once with 200 ml of saturated sodium chloride solution, dried ($MgSO_4$), filtered and evaporated. Chromatography (silica gel, methylene chloride/methanol 19:1) and recrystallization from hexane yielded 34.4 g (88%) of 3-(4-ethyl-3,5-dimethoxy-phenyl)-1-methyl-piperidin-4-one as pale yellow crystals of m.p. 84–85°.

f) A solution of 39 ml (262.4 mmol) of trimethyl phosphonoacetate in 450 ml of tetrahydrofuran was added dropwise at 0° to a suspension of 9.54 g (238.5 mmol) of sodium hydride (55% in mineral oil) in 450 ml of tetrahydrofuran and the mixture was stirred for 30 minutes. Subsequently, the white suspension was treated with a solution of 33.15 g (119.5 mmol) of 3-(4-ethyl-3,5- dimethoxy-phenyl)-1-methyl-piperidin-4-one in 450 ml of tetrahydrofuran and the mixture was stirred at 50° for 2 hours. After cooling to room temperature the mixture was poured on to 500 ml of ice-water and extracted three times with 400 ml of diethyl ether. The organic phases were washed with 400 ml of water and 400 ml of saturated sodium chloride solution, dried ($Na_2SO_4$), filtered and evaporated. Chromatography (silica gel, methylene chloride/methanol 19:1) and recrystalization from hexane yielded 36.33 g (91%) of methyl (E)-[3-(4-ethyl-3,5-dimethoxy-phenyl)-1-methyl-piperidin-4-ylidene]acetate as pale yellow crystals of m.p. 110–112°.

g 1) 25.76 g (1060 mmol) of magnesium shavings were added to a solution of 35.33 g (106 mmol) of methyl (E)-[3-(4-ethyl-3,5-dimethoxy-phenyl)-1-methyl-piperidin-4-ylidene]acetate in 850 ml of methanol and the mixture was stirred at room temperature for 2 hours. The solution was filtered over Dicalite and evaporated. The residue was partitioned between 300 ml of methylene chloride and 500 ml of saturated ammonium chloride solution. The aqueous phase was extracted three times with 250 ml of methylene chloride. The organic phase was dried ($Na_2SO_4$), filtered and evaporated. Chromatography (silica gel, ethyl acetate/methanol/$NH_4OH$ 200:10:1) yielded 7.16 g (20%) of methyl cis-[3-(4-ethyl-3,5-dimethoxy-phenyl)-1-methyl-piperidin-4-yl]-acetate as a colorless oil, Rf=0.23 ((silica gel, ethyl acetate/methanol/$NH_4OH$ 200:10:1) and 23.51 g (66%) of methyl-[3-(4-ethyl-3,5-dimethoxy-phenyl)-1-methyl-piperidin-4-yl]-acetate as a colorless oil, Rf=0.12 (silica gel, ethyl acetatelmethanol/$NH_4OH$ 200:10:1).

g 2) A solution of 11.7 g (35.3 mmol) of methyl (E)-[3-(4-ethyl-3,5-dimethoxy-phenyl)-1-methyl-piperidin-4-ylidene]acetate in 100 ml of methanol was treated with 500 mg of Pd on charcoal and hydrogenated with hydrogen at room temperature for 12 hours. The catalyst was filtered off and the filtrate was evaporated. Chromatography (silica gel, ethyl acetate/methanol/$NH_4OH$ 200:10:1) yielded 9.14 g (77%) of methyl cis-[3-(4-ethyl-3,5-dimethoxy-phenyl)-1-methyl-piperidin-4-yl]-acetate as a colorless oil, Rf=0.23 (silica gel ethyl acetate methanol/$NH_4OH$ 200:10:1) and 2.56 g (21%) of methyl trans-[3-(4-ethyl-3,5-dimethoxy-phenyl)-1-methyl-piperidin-4-yl]-acetate as a colorless oil, Rf=0.12 (silica gel, ethyl acetate/methanol/$NH_4OH$ 200:10:1).

g 3) A solution of 6.4 g (19.3 mmol) of methyl (E)-[3-(4-ethyl-3,5-dimethoxy-phenyl)-1-methyl-piperidin-4-ylidene]acetate in 100 ml of methanol was treated with 1.08 g (20 mmol) of sodium methylate and the mixture was heated at reflux for 6 hours. The solution was evaporated and the residue was partitioned between 50 ml of methyl acetate and 50 ml of water. The organic phases were dried ($MgSO_4$), filtered and evaporated. The colorless oil was dissolved in 50 ml of methanol, treated with 125 mg of Pd on charcoal and hydrogenated with hydrogen at room temperature for 12 hours. The catalyst was filtered off and the filtrate was evaporated. Chromatography (silica gel, ethyl acetate/methanol/$NH_4OH$ 200:10:1) yielded 5.68 g (88%) of methyl cis-[3-(4-ethyl-3,5-dimethoxy-phenyl)-1-methyl-piperidin-4-yl]-acetate as a colorless oil, Rf=0.23 (silica gel, ethyl acetate/methanol/$NH_4OH$ 200:10:1).

h) A mixture of 140 g of polyphosphoric acid and 50 ml of toluene was heated to 120° and treated with a solution of 13.9 g (41.5 mmol) of methyl cis-[3-(4-ethyl-3,5-dimethoxy-phenyl)-1-methyl-piperidin-4-yl]-acetate in 120 ml of toluene. The reaction mixture was stirred at 120° for 3 hours and poured slowly into 500 ml of water at 800. The mixture was adjusted to pH=12 with 28% sodium hydroxide solution and extracted three times with 300 ml of ethyl acetate. The organic phase was dried ($Na_2SO_4$), filtered and evaporated. Chromatography (silica gel, methylene chloride/methanol/$NH_4OH$ 110:10:1) gave 8.64 g (68%) of trans-8-ethyl-7,9-dimethoxy-2-methyl-1,3,4,4a,5,10b-hexahydro-2H-benzo[h]isoquinolin-6-one as a colorless oil, Rf=0.32 (silica gel, methylene chloride/methanol/$NH_4OH$ 110:10:1), which was converted with fumaric acid into the fumarate (1:1) with m.p. 194–195.5°.

i) 3.9 (13 mmol) of trans-8-ethyl-7,9-dimethoxy-2-methyl-1,3,4,4a,5,10b-hexahydro-2H-benzo[h]isoquinolin-6-one were converted with HCl in ethyl acetate into the hydrochloride and the latter was subsequently dissolved in 280 ml of methylene chloride.

The solution was cooled to –70° and treated with 15.4ml of a 1M $BBr_3$solution in methylene chloride. After 15minutes the cooling bath was removed. After the solution had reached room temperature it was stirred for one hour, subsequently poured on to 200 ml of ice/sat. sodium hydrogen carbonate solution and extracted three times with 250 ml of methylene chloride. The organic phases were dried ($Na_2SO_4$), filtered and evaporated. Chromatography (silica gel, methylene chloride/methanol/$NH_4OH$ 110:10:1) yielded 2.50 g (67%) of trans-8-ethyl-7-hydroxy-9-methoxy-2-methyl-1,3,4,4a,5,10b-hexahydro-2H-benzo[h]-isoquinolin-6-one, which was converted with fumaric acid into the fumarate (1:1) with m.p. 201–203°.

EXAMPLE 9 cis-8-Ethyl-7-hydroxy-9-methoxy-2-methyl-1,3,4,4a, 5,10b-hexahydro-2H-benzo[h]isoquinolin-6-one In an analogous manner to that described in Example 1 h) and i), from cis-8-ethyl-7,9-dimethoxy-2-methyl-1,3,4,4a, 5,10b-hexahydro-2H-benzo[h]isoquinolin-6-one there was obtained cis-8-ethyl-7-hydroxy-9-methoxy-2-methyl-1,3,4, 4a,5,10b-hexahydro-2H-benzo[h]isoquinolin-6-one, which was converted with fumaric acid into the fumarate (1:1) with m.p. 221–223°.

EXAMPLE 10 trans-8-Bromo-7-hydroxy-9-methoxy-2-methyl-1,3, 4,4a,5, 10b-hexahydro-2H-benzo[h]isoquinolin-6-one a) 2 ml of 1N NaOH solution were added to a solution of 0.726 g (1.87 mmol) of methyl trans-[3-(4-bromo-3,5-dimethoxy-phenyl)-1-methyl-piperidin-4-yl]-acetate in 3 ml of ethanol and the mixture was stirred at 50° for 30 minutes. The solution was evaporated and the residue was dried in a high vacuum. The thus-obtained sodium salt was suspended in 5 ml of acetonitrile. After the addition of 278 mg (2 mmol) of potassium carbonate the suspension was treated at 0° with 0.913 ml (10 mmol) of phosphorus oxychloride and the mixture was subsequently stirred at 50° for 2 hours. Subsequently, the mixture was poured into 10 ml of water, adjusted to pH=12 with 28% NaOH and extracted three times with 15 ml of ethyl acetate. The organic phase was dried ($Na_2SO_4$), filtered and evaporated. Chromatography (silica gel, methylene chloride/methanol 95:5) yielded 0.385 g (58%) of trans-8-bromo-7,9-dimethoxy-2-methyl-1,3,4,4a,5,10b-hexahydro-2H-benzo[h]

isoquinolin-6-one, which was converted with HCl in methanol into the hydrochloride with m.p. 226–228°.

b) A solution of 0.421 g (1:11 mmol) of trans-8-bromo-7,9-dimethoxy-2-methyl-1,3,4,4a,5,10b-hexahydro-2H-benzo[h] isoquinolin-6-one hydrochloride in 40 ml of methylene chloride was treated at −70° with 1.23 ml of a 1M BBr$_3$ solution in methylene chloride. After 15 minutes the cooling bath was removed. After the solution had reached room temperature it was stirred for one hour, subsequently poured on to 80 ml of ice/sat. sodium hydrogen carbonate solution and extracted three times with 60 ml of methylene chloride. The organic phase was dried (Na$_2$SO$_4$), filtered and evaporated. Chromatography (silica gel, methylene chloride/methanol 9:1) yielded 0.315 g (83%) of trans-8-bromo-7-hydroxy-9-methoxy-2-methyl-1,3,4,4a,5,10b-hexahydro-2H-benzo[h] isoquinolin-6-one, which was converted with HCl in methanol into the hydrochloride with m.p. 257–259°.

The methyl [3-(4-bromo-3,5-dimethoxy-phenyl)-1-methyl-piperidin-4-yl]-acetate used was prepared from 4-bromo-3,5-dimethoxybenzaldehyde in an analogous manner to that described in Example 8a), b), c 1), d), e), f) and g 1).

EXAMPLE 11 trans-7-Hydroxy-9-methoxy-2-methyl-1,3,4,4a,5,10b-hexahydro-2H-benzo[h]isoquinolin-6-one In an analogous manner to that described in Example 8 c1), d), e), f), g 1), h) and i), from methyl (3,5-dimethoxy-phenyl)-acetate there was obtained trans-7-hydroxy-9-methoxy-2-methyl-1,3,4,4a,5,10b-hexahydro-2H-benzo[h] isoquinolin-6-one, which was converted with HCl in methanol into the hydrochloride with m.p. >250°.

EXAMPLE 12 cis-2-Methyl-1,3,4,4a,5.11b-hexahydro-2H-8,10-dioxa-2-aza-cyclopenta[b]phenanthren-6-one In an analogous manner to that described in Example 10 a), from methyl cis-(3-benzo[1,3]dioxol-5-yl-1-methyl-piperidin-4-yl)-acetate there was obtained cis-2-methyl-1,3,4,4a,5,11b-hexahydro-2H-8,10-dioxa-2-aza-cyclopenta[b] phenanthren-6-one, which was converted with fumaric acid into the fumarate (1:0.75) with m.p. >250°.

The methyl cis-(3-benzo[1,3]dioxol-5-yl-1-methyl-piperidin-4-yl)-acetate used was prepared in an analogous manner to that described in Example 8 f) and g 3) from 3-benzo[1,3]dioxol-5-yl-1-methyl-piperidin-4-one.

EXAMPLE 13 cis-9-Methoxy-2-methyl-1,3,4,4a,5,10b-hexahydro-2H-benzo[h]isiquinolin-6-one and cis-7-methoxy-2-methyl-1,3,4,4a,5, 10b-hexahydro-2H-benzo[h]isoquinolin-6-one In an analogous manner to that described in Example 8 f), g 3) and h), from 3-(3-methoxy-phenyl)-1-methyl-piperidin-4-one there were obtained cis-9-methoxy-2-methyl-1,3,4,4a,5, 10b-hexahydro-2H-benzo[h]isoquinolin-6-one and cis-7-methoxy-2-methyl-1,3,4,4a,5,10b-hexahydro-2H-benzo[h] isoquinolin-6-one, which were converted with HCl in methanol into their hydrochlorides with m.p. >250°.

EXAMPLE 14 trans-9-Methoxy-2-methyl-1,3,4,4a,5,10b-hexahydro-2H-benzo[h]isiquinolin-6-one

In an analogous manner to that described in Example 8 f), g 1) and h), from 3-(3-methoxy-phenyl)-1-methyl-piperidin-4-one there was obtained trans-9-methoxy-2-methyl-1,3,4,4a,5,10b-hexahydro-2H-benzo[h]isoquinolin-6-one, which was converted with HCl in methanol into the hydrochloride with m.p. >250°.

EXAMPLE 15 cis-2,9-Dimethyl-1,3,4,4a,5,10b-hexahydro-2H-benzo[h]isiquinolin-6-one

In an analogous manner to that described in Example 8 d) e), f), g 3) and h), from methyl 2-m-tolyl-acrylate there was obtained cis-2,9-dimethyl-1,3,4,4a,5,10b-hexahydro-2H-benzo[h]isoquinolin-6-one, which was converted with HCl in methanol into the hydrochloride with m.p. >250°.

EXAMPLE 16 trans-2,9-Dimethyl-1,3,4,4a,5,10b-hexahydro-2H-benzo[h]isoquinolin-6-one

In an analogous manner to that described in Example 8 d), e), f), g1) and h), from methyl 2-m-tolyl acrylate there was obtained trans-2,9-dimethyl-1,3,4,4a,5,10b-hexahydro-2H-benzo[h]isoquinolin-6-one, which was converted with HCl in methanol into the hydrochloride with m.p. >250°.

EXAMPLE 17 cis-9-Chloro-2-methyl-1,3,4,4a,5,10b-hexahydro-2H-benzo[h]isiquinolin-6-one trans-9-chloro-2-methyl-1,3,4,4a,5,10b-hexahydro-2H-benzo[h]isoquinolin-6-one cis-7-chloro-2-methyl-1,3,4,4a,5,10b-hexahydro-2H-benzo[h]isoquinolin-6-one and trans-7-chloro-2-methyl-1,3,4,4a,5,10b-hexahydro-2H-benzo[h] isoquinolin-6-one In an analogous manner to that described in Example 8 d), e), f), g 1) and h), from methyl 2-(3-chloro-phenyl)-acrylate there were obtained cis-9-chloro-2-methyl-1,3,4,4a,5,10b-hexahydro- 2H-benzo[h]isoquinolin-6-one, trans-9-chloro-2-methyl-1,3,4,4a,5,10b-hexahydro-2H-benzo[h] isoquinolin-6-one, cis-7-chloro-2-methyl-1,3,4,4a,5,10b-hexahydro-2H-benzo[h]isoquinolin-6-one and trans-7-chloro-2-methyl-5 1,3,4,4a,5,10b-hexahydro-2H-benzo[h] isoquinolin-6-one which were converted with HCl in methanol into their hydrochlorides with m.p. >250°.

EXAMPLE 18 trans-8-Fluoro-2-methyl-1,3,4,4a,5,10b-hexahydro-2H-benzo[h]isoquinolin-6-one

In an analogous manner to that described in Example 8 d), e), f), g 1) and h), from methyl 2-(4-fluoro-phenyl)-acrylate there was obtained trans-8-fluoro-2-methyl-1,3,4,4a,5,10b-hexahydro-2H-benzo[h]isoquinolin-6-one, which was converted with HCl in methanol into the hydrochloride with m.p. >250°.

EXAMPLE 19 cis-8-Fluoro-2-methyl-1,3,4,4a,5,10b-hexahydro-2H-benzo[h]isoquinolin-6-one

In an analogous manner to that described in Example 8 d), e), f), g 3) and h), from methyl 2-(4-fluoro-phenyl)-acrylate there was obtained cis-8-fluoro-2-methyl-1,3,4,4a,5,10b- hexahydro-2H-benzo[h]isoquinolin-6-one, which was converted with HCl in methanol into the hydrochloride with m.p. >250°.

EXAMPLE 20 trans-2,8-Dimethyl-1,3,4,4a,5,10b-hexahydro-2H-benzo[h]isoquinolin-6-one

In an analogous manner to that described in Example 8 d), e), f), g 1) and h), from methyl 2-o-tolyl-acrylate there was obtained trans-2,8-dimethyl-1,3,4,4a,5,10b-hexahydro-2H-benzo[h]isoquinolin-6-one, which was converted with HCl in methanol into the hydrochloride with m.p. >250°.

EXAMPLE 21 cis-2,8-Dimethyl-1,3,4,4a,5,10b-hexahydro-2H-benzo[h]isoquinolin-6-one

In an analogous manner to that described in Example 8 d), e), f), g 3) and h), from methyl 2-o-tolyl-acrylate there was obtained cis-2,8-dimethyl-1,3,4,4a,5,10b-hexahydro-2H-benzo[h]isoquinolin-6-one, which was converted with HCl in methanol into the hydrochloride with m.p. >250°.

EXAMPLE 22 trans-8-Methoxy-2-methyl-1,3,4,4a,5,10b-hexahydro-2H-benzo[h]isoquinolin-6-one

In an analogous manner to that described in Example 8 f), g 1) and h), from 3-(4-methoxy-phenyl)-1-methyl-piperidin-4-one there was obtained trans-8-methoxy-2-methyl-1,3,4,4a, 5,10b-hexahydro-2H-benzo[h]isoquinolin-6-one, which was converted with HCl in methanol into the hydrochloride with m.p. 222°.

EXAMPLE 23 cis-8-Methoxy-2-methyl-1,3,4,4a,5,10b-hexahydro-2H-benzo[h]isoquinolin-6-one

In an analogous manner to that described in Example 8 f), g 3) and h), from 3-(4-methoxy-phenyl)-1-methyl-piperidin-4-one there was obtained cis-8-methoxy-2-methyl-1,3,4,4a, 5, 10b-hexahydro-2H-benzo[h]isoquinolin-6-one, which was converted with HCl in methanol into the hydrochloride with m.p. >250°.

EXAMPLE 24 trans-8-Ethyl-2-methyl-1,3,4,4a,5,10b-hexahydro-2H-benzo [h]isoquinolin-6-one

In an analogous manner to that described in Example 8 d), e), f), g 1) and h), from methyl 2-(4-ethyl-phenyl)-acrylate there was obtained trans-8-ethyl-2-methyl-1,3,4,4a,5,10b-hexahydro-2H-benzo[h]isoquinolin-6-one, which was converted with HCl in methanol into the hydrochloride with m.p. 226°.

EXAMPLE 25 cis-8-Ethyl-2-methyl-1,3,4,4a,5,10b-hexahydro-2H-benzo[h]isoquinolin-6-one

In an analogous manner to that described in Example 8 d), e), f), g 3) and h), from 2-(4-ethyl-phenyl)-acrylic acid ester there was obtained cis-8-ethyl-2-methyl-1,3,4,4a,5,10b-hexahydro-2H-benzo[h]isoquinolin-6-one, which was converted with HCl in methanol into the hydrochloride with m.p. >250°.

EXAMPLE 26 trans-8-Chloro-2-methyl-1,3,4,4a,5,10b-hexahydro-2H-benzo-[h]isiquinolin-6-one and cis-8-chloro-2-methyl-1,3,4,4a,5,10 b-hexahydro-2H-benzo[h]isoquinolin-6-one In an analogous manner to that described in Example 8 d), e), f), g 1) and h), from 2-(4-chloro-phenyl)-acrylic acid ester there were obtained trans-8-chloro-2-methyl-1,3,4,4a, 5,10b-hexahydro-2H-benzo[h]isoquinolin-6-one and cis-8-chloro-2-methyl-1,3,4,4a,5,10b-hexahydro-2H-benzo[h]isoquinolin-6-one, which were converted with HCl in methanol into their hydrochlorides with m.p. >250°.

EXAMPLE 27 cis-7,9-Difluoro-2-methyl-1,3,4,4a,5,10b-hexahydro-2H-benzo[h]isiquinolin-6-one

In an analogous manner to that described in Example 8 c 2), d), e), f), g 3) and h), from methyl 3,5-difluorophenyl-acetate there was obtained cis-7,9-difluoro-2-methyl-1,3,4, 4a,5,10b-hexahydro-2H-benzo[h]isoquinolin-6-one, which was converted with HCl in methanol into the hydrochloride with m.p. >230°.

EXAMPLE 28 trans-7,9-Difluoro-2-methyl-1,3,4,4a,5,10b-hexahydro-2H-benzo[h]isiquinolin-6-one In an analogous manner to that described in Example 8 c 2), d), e), f), g 1) and h), from methyl 3,5-difluorophenyl-acetate there was obtained trans-7,9-difluoro-2-methyl-1,3, 4,4a,5,10b-hexahydro-2H-benzo[h]isoquinolin-6-one, which was converted with HCl in methanol into the hydrochloride with m.p. >220°.

EXAMPLE 29 cis-7,9-Dichloro-2-methyl-1,3,4,4a,5,10b-hexahydro-2H-benzo[h]isiquinolin-6-one and trans-7,9-dichloro-2-methyl-1,3,4,4a,5,10b-hexahydro-2H-benzo[h]isiquinolin-6-one In an analogous manner to that described in Example 8 c 2), d), e), f), g 1) and h), from ethyl 3,5-dichlorophenylacetate there were obtained cis-7,9-dichloro-2-methyl-1,3,4,4a,5,10b-hexahydro-2H-benzo[h]isoquinolin-6-one and trans-7,9-dichloro-2-methyl-1,3,4,4a, 5,10b-hexahydro-2H-benzo[h]isoquinolin-6-one, which were converted with HCl in methanol into their hydrochlorides with m.p. >250°.

EXAMPLE 30 trans-9-Fluoro-2-methyl-1,3,4,4a,5,10b-hexahydro-2H-benzo[h]isiquinolin-6-one and trans-7-fluoro-2-methyl-1,3,4,4a,5,10b-hexahydro-2H-benzo[h]isiquinolin-6-one In an analogous manner to that described in Example 8 c 2), d), e), f), g 1) and h), from ethyl 3-fluorophenylacetate there were obtained trans-9-fluoro-2-methyl-1,3,4,4a,5,10b-hexahydro-2H-benzo[h]isoquinolin-6-one and trans-7-fluoro-2-methyl-1,3,4,4a,5,10b-hexahydro-2H-benzo[h]isoquinolin-6-one, which were converted with HCl in methanol into their hydrochlorides with m.p. >250°.

EXAMPLE 31 cis-9-Fluoro-2-methyl-1,3,4,4a,5,10b-hexahydro-2H-benzo[h]isiquinolin-6-one and cis-7-fluoro-2-methyl-1,3,4,4a,5,10b-hexahydro-2H-benzo[h]isiquinolin-6-one In an analogous manner to that described in Example 8 c 2), d), e), f), g 3) and h), from ethyl 3-fluorophenyl acetate there were obtained cis-9-fluoro-2-methyl-1,3,4,4a,5,10b-hexahydro-2H-benzo[h]isoquinolin-6-one and cis-7-fluoro-2-methyl-1,3,4,4a,5,10b-hexahydro-2H-benzo[h]isoquinolin-6-one, which were converted with HCl in methanol into their hydrochlorides with m.p. >250°.

EXAMPLE 32 cis-2-Methyl-8-phenyl-1,3,4,4a,5,10b-hexahydro-2H-benzo[h]isoquinolin-6-one

In an analogous manner to that described in Example 8 c 2), d), e), f), g 3) and h), from methyl (4-phenyl)-phenyl acetate there was obtained cis-2-methyl-8-phenyl-1,3,4,4a,5,10b-hexahydro-2H-benzo[h]isoquinolin-6-one, which was converted with HCl in methanol into the hydrochloride with m.p. >250°.

EXAMPLE 33 trans-2-Methyl-8-phenyl-1,3,4,4a,5,10b-hexahydro-2H-benzo[h]isiquinolin-6-one

In an analogous manner to that described in Example 8 c 2), d), e), f), g 1) and h), from methyl (4-phenyl)-phenyl acetate there was obtained trans-2-methyl-8-phenyl-1,3,4,4a,5,10b-hexahydro-2H-benzo[h]isoquinolin-6-one, which was converted with HCl in methanol into the hydrochloride with m.p. >250°.

EXAMPLE 34 cis-8,9-Difluoro-2-methyl-1,3,4,4a,5,10b-hexahydro-2H-benzo[h]isoquinolin-6-one

In an analogous manner to that described in Example 8 c 2), d), e), f), g 3) and h), from methyl 3,4-difluorophenylacetate there was obtained cis-8,9-difluoro-2-methyl-1,3,4,4a,5,10b-hexahydro-2H-benzo[h]isoquinolin-6-one, which was converted with HCl in methanol into the hydrochloride with m.p. >250°.

EXAMPLE 35 trans-8,9-Difluoro-2-methyl-1,3,4,4a,5,10b-hexahydro-2H-benzo[h]isoquinolin-6-one In an analogous manner to that described in Example 8 c 2), d), e), f), g 1) and h), from methyl 3,3-difluoro-phenyl acetate there was obtained trans-8,9-difluoro-2-methyl-1,3,4,4a,5,10b-hexahydro-2H-benzo[h]isoquinolin-6-one, which was converted with HCl in methanol into the hydrochloride with m.p. >250°.

EXAMPLE 36 cis-10-Fluoro-2-methyl-1,3,4,4a,5,10b-hexahydro-2H-benzo[h]isoquinolin-6-one

In an analogous manner to that described in Example 8 f), g 3) and h), from 3-(2-fluorophenyl)-1-methyl-piperidone there was obtained cis-10-fluoro-2-methyl-1,3,4,4a,5,10b-hexahydro-2H-benzo[h]isoquinolin-6-one, which was converted with HCl in methanol into the hydrochloride with m.p. >220°.

EXAMPLE 37 trans-10-Fluoro-2-methyl-1,3,4,4a,5,10b-hexahydro-2H-benzo[h]isoquinolin-6-one

In an analogous manner to that described in Example 8 f), g 1) and h), from 3-(2-fluorophenyl)-1-methyl-piperidone there was obtained trans-10-fluoro-2-methyl-1,3,4,4a,5,10b-hexahydro-2H-benzo[h]isoquinolin-6-one, which was converted with HCl in methanol into the hydrochloride with m.p. >220°.

EXAMPLE 38 cis-10-Methoxy-2-methyl-1,3,4,4a,5,10b-hexahydro-2H-benzo[h]isiquinolin-6-one and trans-10-methoxy-2-methyl-1,3,4,4a,5,10b-hexahydro-2H-benzo[h]isiquinolin-6-one In an analogous manner to that described in Example 8 d), e), f), g 2) and h), from methyl 2-(2-methoxy-phenyl)-acrylate there were obtained cis-10-methoxy-2-methyl-1,3,4,4a,5,10b-hexahydro-2H-benzo[h]isoquinolin-6-one and trans-10-methoxy-2-methyl-1,3,4,4a,5,10b-hexahydro-2H-benzo[h]isoquinolin-6-one, which were converted with HCl in methanol into their hydrochlorides with m.p. >220°.

EXAMPLE 39 cis-2,10-Dimethyl-1,3,4,4a,5,10b-hexahydro-2H-benzo[h]isiquinolin-6-one

In an analogous manner to that described in Example 8 d), e), f), g 3) and h), from methyl 2-(2-methyl-phenyl)-acrylate there was obtained cis-2,10-dimethyl-1,3,4,4a,5,10b-hexahydro-2H-benzo[h]isoquinolin-6-one, which was converted with HCl in methanol into the hydrochloride with m.p. >220°.

EXAMPLE 40 trans-2,10-Dimethyl-1,3,4,4a,5,10b-hexahydro-2H-benzo[h]isiquinolin-6-one

In an analogous manner to that described in Example 8 d), e), f), g 1) and h), from methyl 2-(2-methyl-phenyl)-acrylate there was obtained trans-2,10-dimethyl-1,3,4,4a,5,10b-hexahydro-2H-benzo[h]isoquinolin-6-one, which was converted with HCl in methanol into the hydrochloride with m.p. >220°.

EXAMPLE 41 trans-2,7,9-Trimethyl-1,3,4,4a,5,10b-hexahydro-2H-benzo[h]isiquinolin-6-one

In an analogous manner to that described in Example 8 c 2), d), e), f), g 3) and h), from methyl (3,5-dimethyl-phenyl)-acetate there was obtained trans-2,7,9-trimethyl-1,3,4,4a,5,10b-hexahydro-2H-benzo[h]isoquinolin-6-one, which was converted with HCl in methanol into the hydrochloride with m.p. >250°.

EXAMPLE 42 cis-2,7,9-Trimethyl-1,3,4,4a,5,10b-hexahydro-2H-benzo[h]isiquinolin-6-one

In an analogous manner to that described in Example 8 c 2), d), e), f), g 1) and h), from methyl (3,5-dimethyl-phenyl)-acetate there was obtained cis-2,7,9-trimethyl-1,3,4,4a,5,10b-hexahydro-2H-benzo[h]isoquinolin-6-one, which was converted with HCl in methanol into the hydrochloride with m.p. >250°.

EXAMPLE 43

(−)-trans-8-Ethyl-7-hydroxy-9-methoxy-2-methyl-1,3,4,4a,5, 10b-hexahydro-2H-benzo[h]isiquinolin-6-one (+)-trans-8-Ethyl-7-hydroxy-9-methoxy-2-methyl-1,3,4,4a,5, 10b-hexahydro-2H-benzo[h]isiquinolin-6-one 3.08 g (8.6 mmol) of (+)-O,O-dibenzoyltartaric acid were added to a solution of 2.58 g (8.6 mmol) of trans-8-ethyl- 7-hydroxy-9-methoxy-2-methyl-1,3,4,4a,5,10b-hexahydro-2H-benzo[h]isoquinolin-6-one in 40 ml of ethanol and the mixture was stirred at room temperature for 15 minutes. Subsequently, it was heated to reflux and sufficient ethanol was added thereto in order to give a clear solution (about 80 ml). After cooling to room temperature the resulting crystals (2.52 g) were filtered off and dissolved in a mixture of 50 ml of methylene chloride and 50 ml of 2N sodium carbonate solution. The sodium carbonate solution was washed once with methylene chloride. The organic phases were dried ($MgSO_4$), filtered and evaporated. The yellow oil obtained (1.18 g) was converted with HCl in methanol into the hydrochloride. After recrystallization from diisopropyl ether/ethanol there was obtained 0.86 g of (+)-trans-8-ethyl-7-hydroxy-9-methoxy-2-methyl-1,3,4,4a,5,10b-hexahydro-2H-benzo[h]isoquinolin-6-one hydrochloride with m.p. 261–263, $[\alpha]_{589}$=+28.6 (c=0.5, $H_2O$).

The mother liquor of the crystallization with (+)-O,O-dibenzoyltartaric acid was evaporated and the residue was partitioned between methylene chloride and a 2N sodium carbonate solution. The aqueous phase was washed twice with methylene chloride and the organic phases were dried ($MgSO_4$), filtered and evaporated. The thus-obtained light yellow oil (1.39 g (4.8 mmol)) was dissolved in 20 ml of ethanol and treated with 1.72 g (4.8 mmol) of (−)-O,O'-dibenzoyltartaric acid. Subsequently, the mixture was heated to reflux and sufficient ethanol was added thereto to give a clear solution (about 40 ml). After cooling to room temperature the resulting crystals (2.26 g) were filtered off and dissolved in a mixture of 50 ml of methylene chloride and 50 ml of 2N sodium carbonate solution. The sodium carbonate solution was washed once with methylene chloride. The organic phases were dried ($MgSO_4$), filtered and evaporated. The thus-obtained yellow oil (1.22 g) was converted with HCl in methanol into the hydrochloride. After recrystallization from diisopropyl ether/ethanol there was obtained 0.82 g of (−)-trans-8-ethyl-7-hydroxy-9-methoxy-2-methyl-1,3,4,4a,5,10b-hexahydro-2H-benzo[h]isoquinolin-6-onehydrochloride with m.p. 261–263°, $[\alpha]_{589}$=−29.2 (c=0.5, $H_2O$).

EXAMPLE 44

(+)-cis-7-Methoxy-2-methyl-1,3,4,4a,5,10b-hexahydro-2H-benzo[h]isiquinolin-6-one (−)-cis-7-Methoxy-2-methyl-1,3,4,4a,5,10b-hexahydro-2H-benzo[h]isiquinolin-6-one In an analogous manner to that described in Example 43, from cis-7-methoxy-2-methyl-1,3,4,4a,5,10b-hexahydro-2H-benzo[h]isoquinolin-6-one by crystallization with (+)-O,O-dibenzoyltartaric acid there was obtained (+)-cis-7-methoxy-2-methyl-1,3,4,4a,5,10b-hexahydro-2H-benzo[h]isoquinolin-6-one, which was converted with HCl in methanol into the hydrochloride. After recrystallization from ethanol there was obtained (+)-cis-7-methoxy-2-methyl-1,3,4,4a,5,10b-hexahydro-2H-benzo[h]isoquinolin-6-one hydrochloride with m.p. >250°, $[\alpha]_{589}$=+2.6 (c=0.5, $H_2O$).

By crystallization with (−)-O,O-dibenzoyltartaric acid there was obtained (−)-cis-7-methoxy-2-methyl-1,3,4,4a,5,10b-hexahydro-2H-benzo[h]isoquinolin-6-one, which was converted with HCl in methanol into the hydrochloride. After recrystallization from ethanol there was obtained (−)-cis-7-methoxy-2-methyl-1,3,4,4a,5, 10b-hexahydro-2H-benzo[h]isoquinolin-6-one hydrochloride with m.p. >2500, $[\alpha]_{589}$=−2.4 (c=0.5, $H_2O$).

EXAMPLE 45

(−)-trans-7-methoxy-2-methyl-1,3,4,4a,5,10b-hexahydro-2H-benzo[h]isoquinolin-6-one In an analogous manner to that described in Example 43, from trans-7-methoxy-2-methyl-1,3,4,4a,5,10b-hexahydro-2H-benzo[h]isoquinolin-6-one by crystallization with (+)-O,O'-dibenzoyltartaric acid there was obtained (+)-trans-7-methoxy-2-methyl-1,3,4,4a,5,10b-hexahydro-2H-benzo[h]isoquinolin-6-one, which was converted with HCl in methanol into the hydrochloride. After recrystallization from ethanol there was obtained (+)-trans-7-methoxy-2-methyl-1,3,4,4a,5,10b-hexahydro-2H-benzo[h]isoquinolin-6-one hydrochloride with m.p. >250, $[\alpha]_{589}$=+39.5 (c=0.5, methanol).

By crystallization with (−)-O,O'-dibenzoyltartaric acid there was obtained (−)-cis-7-methoxy-2-methyl-1,3,4,4a,5,10b-hexahydro-2H-benzo[h]isoquinolin-6-one, which was converted with HCl in methanol into the hydrochloride. After recrystallization from ethanol there was obtained (−)-trans-7-methoxy-2-methyl-1,3,4,4a,5,10b-hexahydro-2H-benzo[h]isoquinolin-6-one hydrochloride with m.p. >250°, $[\alpha]_{589}$=−41.2 (c=0.5, methanol).

EXAMPLE 46

(+)-cis-2,7-Dimethyl-1,3,4,4a,5,10b-hexahydro-2H-benzo[h]isiquinolin-6-one (−)-cis-2,7-Dimethyl-1,3,4,4a,5,10b-hexahydro-2H-benzo[h]isiquinolin-6-one In an analogous manner to that described in Example 43, from cis-2,7-dimethyl-1,3,4,4a,5,10b-hexahydro-2H-benzo[h]isoquinolin-6-one by crystallization with (+)-O,O-dibenzoyltartaric acid there was obtained (+)-cis-2,7-dimethyl-1,3,4,4a,5,10b-hexahydro-2H-benzo[h]isoquinolin-6-one, which was converted with fumaric acid in ethanol into the fumarate.

After recrystallization from ethanol there was obtained (+)-cis-2,7-dimethyl-1,3,4,4a,5,10b-hexahydro-2H-benzo[h]isoquinolin-6-one fumarate (1:1) with m.p. 230.5–232°, $[\alpha]_{589}$=+6.8 (c=0.5, $H_2O$).

By crystallization with (−)-O,O-dibenzoyltartaric acid there was obtained (−)-cis-2,7-dimethyl-1,3,4,4a,5,10b-hexahydro-2H-benzo[h]isoquinolin-6-one, which was converted with fumaric acid in ethanol into the fumarate. After recrystallization from ethanol there was obtained (−)-cis-2,7-dimethyl-1,3,4,4a,5,10b-hexahydro-2H-benzo[h]isoquinolin-6-one fumarate (1:1) with m.p. 230.5–232°, $[\alpha]_{589}$=−5.6 (c=0.5, $H_2O$).

EXAMPLE 47

(+)-cis-2,7,9-Trimethyl-1,3,4,4a,5,10b-hexahydro-2H-benzo[h]isiquinolin-6-one (−)-cis-2,7.7-Trimethyl-1,3,4,4a,5,10b-hexahydro-2H-benzo[h]isiquinolin-6-one In an analogous manner to that described in Example 43, from cis-2,7,9-trimethyl-1,3,4,4a,5,10b-hexahydro-2H-benzo[h]isoquinolin-6-one by crystallization with (+)-O,O'-dibenzoyltartaric acid there was obtained (+)-cis-2,7,9-trimethyl-1,3,4,4a,5,10b-hexahydro-2H-benzo[h]isoquinolin-6-one, which was converted with fumaric acid in ethanol into the fumarate. After recrystallization from ethanol there was obtained (+)-cis-2,7,9-trimethyl-1,3,4,4a,5,10b-hexahydro-2H-benzo[h]isoquinolin-6-one fumarate (1:1) with m.p. 219–220°, $[\alpha]_{589}$=+22.8 (c=0.5, $H_2O$).

By crystallization with (−)-O,O-dibenzoyltartaric acid there was obtained (−)-cis-2,7,7-trimethyl-1,3,4,4a,5,10b-hexahydro-2H-benzo[h]isoquinolin-6-one, which was converted with fumaric acid in ethanol into the fumarate. After recrystallization from ethanol there was obtained (−)-cis-2,7,9-trimethyl-1,3,4,4a,5,10b-hexahydro-2H-benzo[h]isoquinolin-6-one fumarate (1:1) with m.p. 219–220°, $[\alpha]_{589}$=−22.8 (c=0.5, $H_2O$).

EXAMPLE 48

(−)-cis-2-Methyl-1,3,4,4a,5,10b-hexahydro-2H-benzo[h]isoquinolin-6-one (+)-cis-2-Methyl-1,3,4,4a,5,10b-hexahydro-2H-benzo[h]isoquinolin-6-one In an analogous manner to that described in Example 43, from cis-2-methyl-1,3,4,4a,5,10b-hexahydro-2H-benzo[h]-isoquinolin-6-one by crystallization with (−)-O,O'-di-p-toluoyltartaric acid there was obtained (−)-cis-2-methyl-1,3,4,4a,5,10b-hexahydro-2H-benzo[h]isoquinolin-6-one, which was converted with fumaric acid in ethanol into the fumarate. After recrystallization from ethanol there was obtained (−)-cis-2-methyl-1,3,4,4a,5,10b-hexahydro-2H-benzo[h]isoquinolin-6-one fumarate (1:1) with m.p. 206.5–208.5°, $[\alpha]_{589}$=−21.6 (c=0.5, $H_2O$).

By crystallization with (+)-O,O'-di-p-toluoyltartaric acid there was obtained (+)-cis-2-methyl-1,3,4,4a,5,10b-hexahydro-2H-benzo[h]isoquinolin-6-one, which was converted with fumaric acid in ethanol into the fumarate. After recrystallization from ethanol there was obtained (+)-cis-2-methyl-1,3,4,4a,5,10b-hexahydro-2H-benzo[h]isoquinolin-6-one fumarate (1:1) with m.p. 207–209°, $[\alpha]_{589}$=+20.8 (c=0.5, $H_2O$).

EXAMPLE 49 cis-8-Fluoro-2-propyl-1,3,4,4a,5,10b-hexahydro-2H-benzo[h]-isoquinolin-6-one a) 0.45 g (1.92 mmol) of 8-fluoro-2-methyl-1,3,4,4a,5,10b-hexahydro-2H-benzo[h]isoquinolin-6-one was dissolved in 6 ml of anhydrous chloroform and added dropwise at room temperature over 15 minutes to a solution of 244 mg (2.3 mmol) of cyanogen bromide in 2 ml of anhydrous chloroform. Subsequently, the mixture was heated under reflux for a further 75 minutes, concentrated in a vacuum, taken up with 12 ml of 2N hydrochloric acid and heated under reflux over 6 hours. Subsequently, the mixture was made basic with 3N sodium hydroxide solution and extracted three times with 50 ml of diethyl ether each time. The combined organic phases were washed once with 70 ml of saturated sodium chloride solution, dried ($MgSO_4$) and concentrated in a vacuum. 0.29 g (69%) of cis-8-fluoro-1,3,4,4a,5,10b-hexahydro-2H-benzo[h]isoquinolin-6-one was obtained as a yellow oil.

b) A mixture of 0.29 g (1.32 mmol) of cis-8-fluoro-1,3,4,4a,5,10b-hexahydro-2H-benzo[h]isoquinolin-6-one, 0.12 ml (1.39 mmol) of bromopropane, 0.2 g (1.45 mmol) of potassium carbonate and 20 ml of anhydrous DMF was heated to 125° C. for 1 hour. Subsequently, the mixture was poured into 3 ml of water and extracted once with 50 ml of ethyl acetate. The organic phase was washed once with 40 ml of saturated sodium chloride solution, dried ($MgSO_4$) and concentrated in a vacuum. The crude product obtained was purified by column chromatography on silica gel (methylene chloride/methanol/$NH_4OH$ 9:1:0.2). There were obtained 220 mg (63%) of cis-8-fluoro-2-propyl-1,3,4,4a, 5,10b-hexahydro-2H-benzo[h] isoquinolin-6-one as a yellow oil, which was converted with MeOH/HCl into the hydrochloride with m.p. >220°.

EXAMPLE 50 cis-8-Fluoro-2-ethyl-1,3,4,4a,5,10b-hexahydro-2H-benzo[h]isiquinolin-6-one

In an analogous manner to that described in Example 49 b), from cis-8-fluoro-1,3,4,4a,5,10b-hexahydro-2H-benzo[h]isoquinolin-6-one by alkylation with ethyl bromide there was obtained cis-8-fluoro-2-ethyl-1,3,4,4a,5,10b-hexahydro-2H-benzo[h]isoquinolin-6-one, which was converted with MeOH/HCl into the hydrochloride with m.p. >220°.

EXAMPLE 51 cis-2-Benzyl-8-fluoro-1,3,4,4a,5,10b-hexahydro-2H-benzo[h]isoquinolin-6-one

In an analogous manner to that described in Example 49 b), from cis-8-fluoro-1,3,4,4a,5,10b-hexahydro-2H-benzo[h]isoquinolin-6-one by alkylation with benzyl bromide there was obtained cis-2-benzyl-8-fluoro-1,3,4,4a,5,10b-hexahydro-2H-benzo[h]isoquinolin-6-one, which was converted with MeOH/HCl into the hydrochloride with m.p. >220°.

EXAMPLE 52

(+)-7,9-Dimethyl-2-propyl-1,3,4,4a,5,10b-hexahydro-2H-benzo[h]isoquinolin-6-one

In an analogous manner to that described in Example 49 b), from (+)-7,9-dimethyl-1,3,4,4a,5,10b-hexahydro-2H-benzo[h]isoquinolin-6-one by alkylation with bromopropane there was obtained (+)-7,9-dimethyl-2-propyl-1,3,4,4a,5,10b-hexahydro-2H-benzo[h]isoquinolin-6-one, which was converted with fumaric acid into the fumarate (1:1) with m.p. 220.5–226.50°, $[\alpha]_{589}$=+33.7 (c=0.5, $H_2O$).

The (+)-7,9-dimethyl-1,3,4,4a,5,10b-hexahydro-2H-benzo[h]isoquinolin-6-one used was prepared as follows:

a 2.1) 0.76 ml (5.65 mmol) of 2,2,2-trichloroethyl chloroformate was added at 1000 to a suspension of 500 mg (2.26 mmol) of (+)-cis-2,7,9-trimethyl-1,3,4,4a,5,10b-hexahydro-2H-benzo[h]isoquinolin-6-one and 120 mg of $K_2CO_3$ in 20 ml of toluene and the mixture was heated at reflux for 16 hours. Subsequently, the solution was cooled to room temperature and poured on to 40 ml of ice-water. The aqueous phase was extracted twice with 50 ml of ethyl acetate, dried ($MgSO_4$), filtered and evaporated. Chromatography of the residue (silica gel, hexane/ethyl acetate 4:1) yielded 890 mg (97%) of 2,2,2-trichloroethyl 7,9-dimethyl-6-oxo-3,4,4a,5,6,10b-hexahydro-1H-benzo [h]isoquinoline-2-carboxylate as a colorless oil.

a 2.2) 250 mg of Zn powder were added to a solution of 890 mg (2.2 mmol) of 2,2,2-trichloroethyl 7,9-dimethyl-6-oxo-3,4,4a,5, 6,10b-hexahydro-1H-benzo[h]isoquinoline-2-carboxylate in 10 ml of glacial acetic acid and the mixture was stirred at room temperature for 16 hrs. The solution was filtered and adjusted to pH 10 with 28% NaOH. The aqueous phase was extracted twice with the 30 ml of methylene chloride, dried ($Na_2SO_4$), filtered and evaporated. Chromatography of the residue (silica gel, methylene chloride/methanol/$NH_4OH$ 200:10:1) yielded 420 mg (83%) of 7,9-dimethyl-1,3,4,4a,5,10b-hexahydro-2H-benzo[h]isoquinolin-6-one as a colorless oil.

EXAMPLE A

Tablets of the following composition are produced in the usual manner:

|  | mg/tablet |
| --- | --- |
| Active ingredient | 100 |
| Powd. lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE B

Tablets of the following composition are produced in the usual manner:

|  | mg/tablet |
| --- | --- |
| Active ingredient | 200 |
| Powd. lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE C

Capsules of the following composition are produced:

|  | mg/capsule |
| --- | --- |
| Active ingredient | 50 |
| Cryst. lactose | 60 |
| Microcrystalline cellulose | 34 |
| Talc | 5 |
| Magnesium stearate | 1 |
| Capsule fill weight | 150 |

The active substance having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

What is claimed is:

1. A compound of the formula

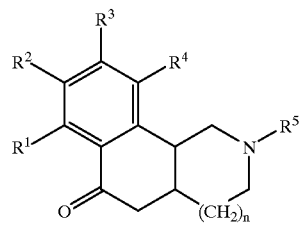

wherein
$R^1$–$R^4$ each independently signify hydrogen, halogen, hydroxy, lower alkyl, lower alkoxy or phenyl or $R^2$ and $R^3$ together represent —O—$CH_2$—O—;
$R^5$ signifies hydrogen, lower alkyl or benzyl; and
n signifies 0,
or a pharmaceutically acceptable acid addition salt of the compound of formula I.

2. The compound according to claim 1, rac-cis-7-ethyl-6-hydroxy-8-methoxy-2-methyl-1,2,3,3a,4,9b-hexahydro-benzo[e]isoindol-5-one.

3. The compound according to claim 1, rac-cis-7-ethyl-6,8-dimethoxy-2-methyl-1,2,3,3a,4,9b-hexahydro-benzo[e]isoindol-5-one.

4. The compound according to claim 1, rac-cis-8-methoxy-2-methyl-1,2,3,3a,4,9b-hexahydro-benzo[e]isoindol-5-one.

5. The compound according to claim 1, rac-cis-2,8-Dimethyl-1,2,3,3a,4,9b-hexahydro-benzo[e]isoindol-5-one.

6. The compound according to claim 1, rac-cis-8-chloro-2-methyl-1,2,3,3a,4,9b-hexahydro-benzo[e]isoindol-5-one.

7. The compound according to claim 1, rac-cis-2-methyl-1,2,3,3a,4,9b-hexahydro-benzo[e]isoindol-5-one.

8. The compound according to claim 1, rac-cis-7-methoxy-2-methyl-1,2,3,3a,4,9b-hexahydro-benzo[e]isoindol-5-one.

9. A compound, cis-2-Methyl-1,3,4,4a,5,11b-hexahydro-2H-8,10-dioxa-2-aza-cyclopenta[b]phenanthren-6-one.

10. A compound, rac-cis-8-fluoro-2-propyl-1,3,4,4a,5,10b-hexahydro-2H-benzo[h]isoquinolin-6-one, or the pharmaceutically acceptable salts thereof.

11. A compound, rac-cis-8-fluoro-2-ethyl-1,3,4,4a,5,10b-hexahydro-2H-benzo[h]isoquinolin-6-one, or the pharmaceutically acceptable salts thereof.

12. A compound, rac-cis-2-benzyl-8-fluoro-1,3,4,4a,5,10b-hexahydro-2H-benzo[h]isoquinolin-6-one, or the pharmaceutically acceptable salts thereof.

13. A compound, rac-(+)-7,9-dimethyl-2-propyl-1,3,4,4a,5,10b-hexahydro-2H-benzo[h]isoquinolin-6-one or the pharmaceutically acceptable salts thereof.

* * * * *